HONEY LOCUST TREE
Filed Nov. 5, 1970 2 Sheets-Sheet 1
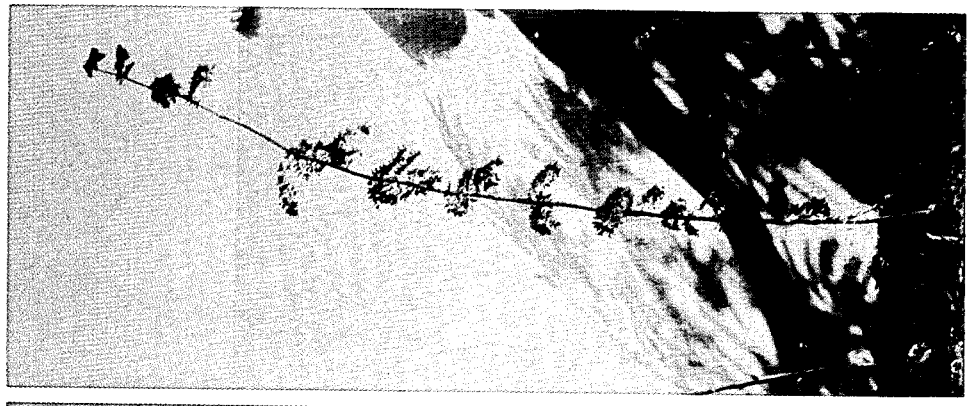
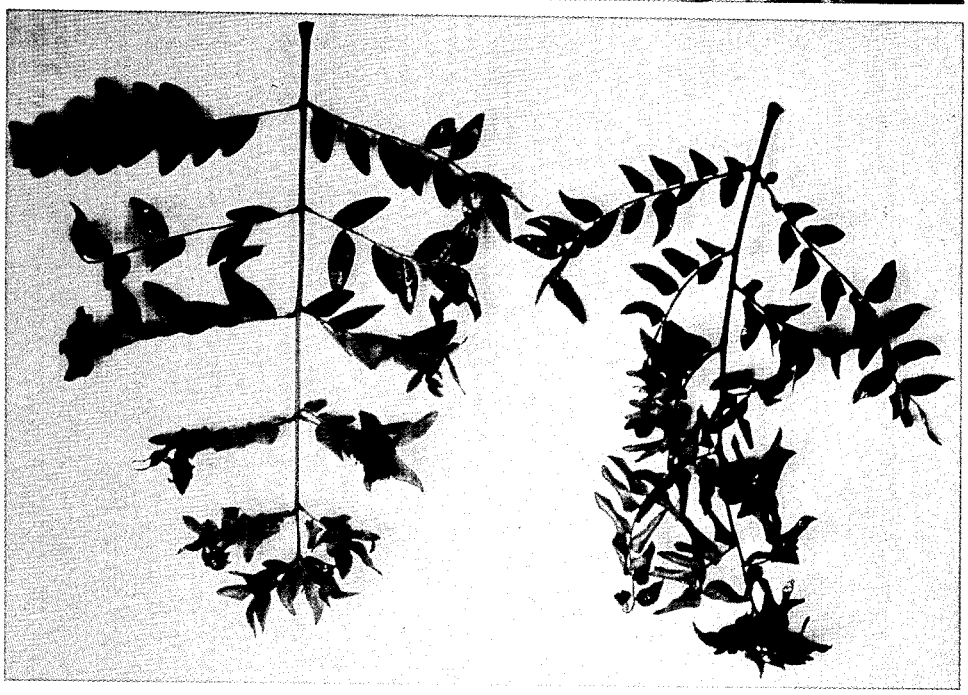
Inventor.
J. H. Mc Intyre
By: Robb & Robb
Attorneys.

HONEY LOCUST TREE
Filed Nov. 5, 1970 2 Sheets-Sheet 2
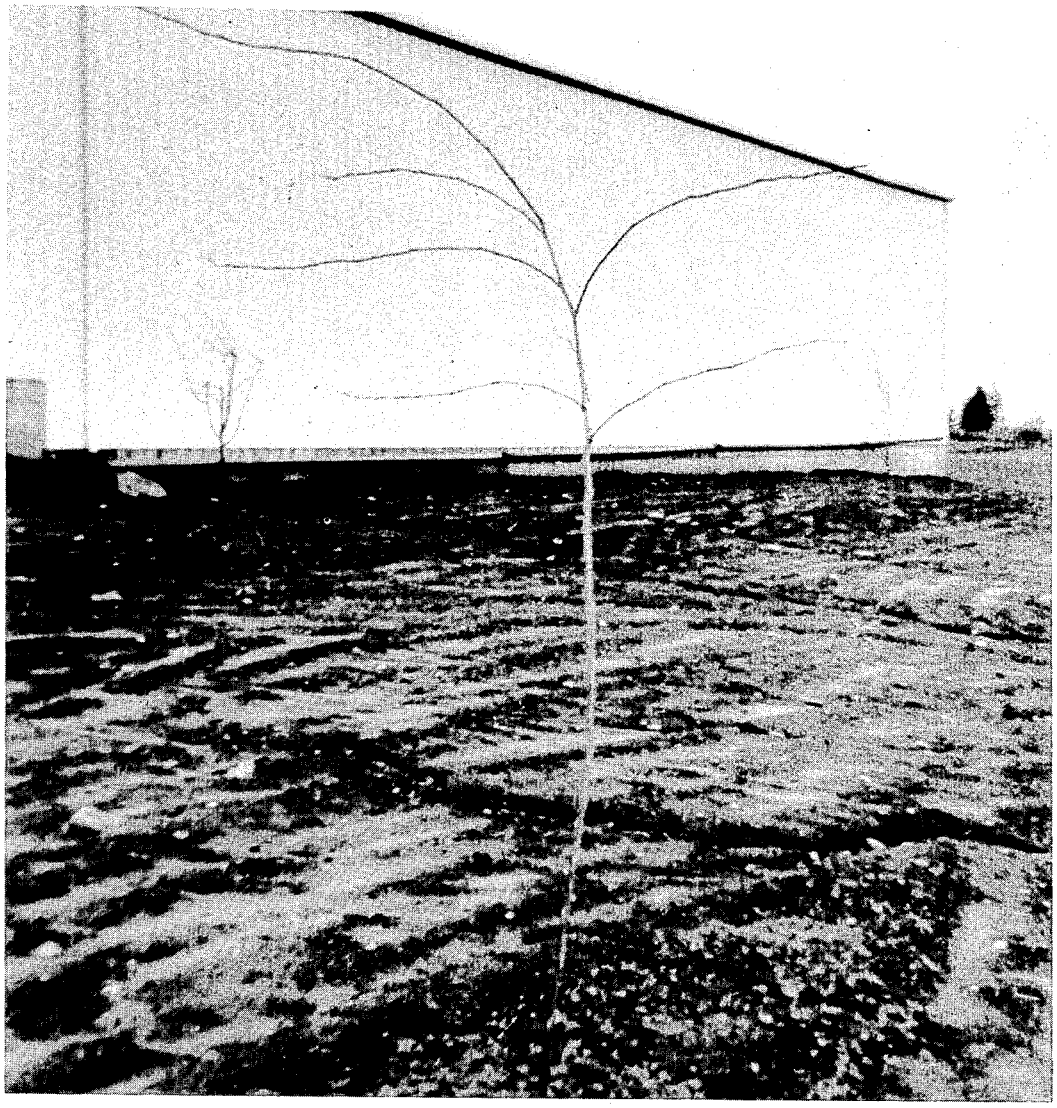

United States Patent Office

Plant Pat. 3,260
Patented Aug. 22, 1972

3,260

HONEY LOCUST TREE

John H. McIntyre, Gresham, Oreg., assignor to The W. E. McGill Trust, doing business as A. McGill and Son, Fairview, Oreg.

Filed Nov. 5, 1970, Ser. No. 87,365
Int. Cl. A01h *5/00*
U.S. Cl. Plt.—52 1 Claim

The present invention relates to a new and distinct variety of honey locust tree which was discovered by me on the cultivated nursery property of my assignee at Fairview, Oreg., as a newly found seedling of an unnamed and unpatented variety of the species botanically known as *Gleditsia triacanthos inermis.*

At the time of my discovery aforesaid, a field of seedlings had been planted and were being grown under my direction and supervision for use as understock. During these growing operations, my attention was attracted to one particular seedling which bore darker colored foliage than was the average color of the other seedlings, and also by the fact that the leaves were carried at a more upright angle than the average on the other seedlings. Continued observations and tests of the new seedling, as well as progeny thereof derived by buddings made by me in the nursery aforementioned confirmed that these features, among others later observed, were established and represent a new honey locust variety which is distinguished from all other varieties of this species of which I am aware, as evidenced by the following unique combination of characteristics which are outstanding in the new seedling:

(1) A strong growing habit which makes the trees approximately 20% taller than is average for the species in the first year of growth and continuing to grow faster in succeeding years, as determined by comparison with other varieties of the same species grown on the same root-stock in the same fields;
(2) A habit of carrying the leaflets at a more acute angle in a plane at right angles to the stem than is normal for the species;
(3) A twisted form of the leaflets when young and until they mature, giving the leaves a ruffled or rippled appearance; and
(4) A distinctive, attractive and darker green leaf color than is average for the species.

The accompanying drawings show a typical young tree specimen about one year old and typical foliage specimens on a somewhat larger scale than in the view of the tree specimen, all as depicted in color as nearly true as it is reasonably possible to make the same in an illustration of this type. The drawings also show in black and white a typical three-year-old bare tree specimen illustrating the general form of the tree.

The following is a detailed description of my new variety of honey locust tree, with color terminology in accordance with the Exotica Horticultural Color Guide, published by Roehrs Company, of Rutherford, N.J.:

Parentage: An unnamed seedling of the species *Gleditsia triacanthos inermis.*
Propagation: Holds its distinguishing characteristics through propagations by budding.
Locality where grown and observed: Fairview, Oreg.
Tree: Large; spreading; tall; hardy.
*Trunk.*—Smooth.
*Branches.*—Slender; smooth. Color—Olive Green, Color No. 84. Lenticels—average number of the species.
Foliage:
*Leaves.*—Compound; leaves range from 5 cm. to 15 cm. long and from 4 cm. to 12 cm. wide; leaves are both pinnate and bipinnate; from 20 to 24 leaflets when pinnate and from 8 to 12 pinnae when bipinnate, with from 10 to 14 leaflets per pinnae; Quantity—profuse.
*Leaflets.*—Size—medium. Length—about 2.2 cm. Width—about 0.8 cm. Shape—ovate oblong. Color—upper surface—Ivy Green, Color No. 70. under surface—Fern Green, Color No. 83. Margin—remotely crenate—serrate; slightly ruffled. Petiole—short. Leaf glands—none. Substance and aspect—thick; tough; smoothness and glossiness comparable to average for the species.
Flower buds: None observed; probably sterile.
Flowers: None observed.

I claim:

1. A new and distinct variety of honey locust tree of the species botanically known as *Gleditsia triacanthos inermis,* substantially as herein shown and described, characterized particularly as to novelty by the unique combination of a strong growing habit which makes the trees approximately 20% taller than is average for the species in the first year of growth and continuing thereafter, a habit of carrying the leaflets at a more acute angle to the stem in a plane at right angles to the stem than is normal for the species, a twisted form of the leaflets when young and until they mature which gives the leaves a ruffled or rippled appearance, and a distinctive, attractive and darker green leaf color than is average for the species.

References Cited

UNITED STATES PATENTS

P.P. 2,786 1/1968 Synnestvedt -------- Plants—52

ROBERT E. BAGWILL, Primary Examiner